United States Patent
Cattuzzato et al.

(10) Patent No.: US 9,687,431 B2
(45) Date of Patent: Jun. 27, 2017

(54) USE OF ISOLEUCINE N-HEXADECANOYL AS A "VOLUMIZING" AND/OR "PLUMPING" AGENT FOR HUMAN SKIN

(75) Inventors: Laetitia Cattuzzato, Castres (FR); Nathalie Chevrot, Paris (FR); Sandy Dumont, Caucalieres (FR); Corinne Stoltz, Thiais (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 911 days.

(21) Appl. No.: 13/383,934

(22) PCT Filed: Jul. 22, 2010

(86) PCT No.: PCT/FR2010/051550
§ 371 (c)(1),
(2), (4) Date: Jan. 13, 2012

(87) PCT Pub. No.: WO2011/015758
PCT Pub. Date: Feb. 10, 2011

(65) Prior Publication Data
US 2012/0115956 A1    May 10, 2012

(30) Foreign Application Priority Data
Jul. 28, 2009   (FR) .................................. 09 55289

(51) Int. Cl.
*A61K 8/44* (2006.01)
*A61Q 19/06* (2006.01)
*A61Q 19/08* (2006.01)

(52) U.S. Cl.
CPC ............... *A61K 8/44* (2013.01); *A61Q 19/06* (2013.01); *A61Q 19/08* (2013.01)

(58) Field of Classification Search
None
See application file for complete search history.

(56) References Cited

FOREIGN PATENT DOCUMENTS

| FR | 2873575 | 2/2006 |
|---|---|---|
| FR | 2873575 A1 * | 2/2006 |
| GB | 1436614 | 5/1976 |
| JP | 2003096039 | 4/2003 |
| WO | 90/14429 | 11/1990 |
| WO | WO 9014429 A1 * | 11/1990 |
| WO | 98/09611 | 3/1998 |
| WO | 2008/015639 | 2/2008 |

OTHER PUBLICATIONS

Yu et al., "Chronological Changes in Metabolism and Functions of Cultured Adipocytes: a Hypothesis for Cell Aging in Mature Adipocytes", Am J Physiol Endocrinol Metab 286, 2004, pp. 402-410, Cited in specification.
Guo et al., "Aging Results in Paradoxical Susceptibility of Fat Cell Progenitors to Lipotoxicity", Am J Physiol Endocrinol Metab 292, 2007, pp. 1041-1051, Cited in specification.
Gregoire et al., "Understanding Adipocyte Differentiation", Physiological Reviews, Jul. 1998, pp. 783-809, vol. 78, No. 3, Cited in specification.
Smith et al., "The Adipocyte Life Cycle Hypothesis", Clinical Science, 2006, pp. 1-9, vol. 110, Cited in specification.
Dumont et al., "Analysis of the Implications of the Adipose Tissue in Facial Morphology, from a Revue of the Literature and Dissections of 10 Half-Faces", Annales de Chirurgie Esthetique 52, 2007, pp. 196-205, Cited in specification.
Karagiannides et al., "Altered Expression of C/EBP Family Members Results in Decreased Adipogenesis with Aging", Am J Physiol Regulatory Integrative Comp Physiol 280, 2001, pp. 1772-1780, Cited in specification.
Karagiannides et al., "Increased CUG Triplet Repeat-binding Protein-1 Predisposes to Impaired Adipogenesis with Aging", The Journal of Biological Chemistry, Aug. 2006, pp. 23025-23033, vol. 281, No. 32, Cited in specification.
Kirkland et al., "Adipogenesis and Aging: Does Aging Make Fat Go Mad?", Experimental Gerontology 37, 2002, pp. 757-767, Cited in specification.
Database WPI Week 200355, Thomson Scientific, London, GB, AN 2003-581051, XP002570458, Cited in FR Search Report.
French Search Report dated Mar. 4, 2010 from FR0955289.
International Search Report dated Aug. 24, 2011 from international application PCT/FR2010/051550.

* cited by examiner

Primary Examiner — Svetlana M Ivanova
(74) Attorney, Agent, or Firm — Young & Thompson

(57) ABSTRACT

The invention relates to the cosmetic use of isoleucine N-hexadecanoyl of formula (I): $CH_3-(CH_2)_{14}-C(=O)-NH-CH(COOH)-CH(CH_3)-CH_2-CH_3$ (I) as a "volumizing" agent and/or as a "plumping" agent for human skin. The invention also relates to a cosmetic treatment method for obtaining a "volumizing" and/or "plumping" effect of the skin of a part of the human body selected from among the breasts, face, cheeks, buttocks and eyelids.

1 Claim, No Drawings

USE OF ISOLEUCINE N-HEXADECANOYL AS A "VOLUMIZING" AND/OR "PLUMPING" AGENT FOR HUMAN SKIN

The present invention relates to the field of cosmetic and pharmaceutical active ingredients and also to the topical compositions comprising same.

The increase in life expectancy in developed countries has been constantly accompanied by a desire for "rejuvenation" which has become more pronounced over the past thirty years or so. This wish is reflected by attempts to delay the phenomenon of slackening of the skin in aging adults, which is reflected, in particular on the face, by a modification of the features and expressions of individuals. Within the same context of preserving a "young" dynamic look and a shapely figure, visibly reflecting well-being, some women are also looking for solutions intended to firm the bust or even increase the volume thereof. This behavioral change has been accompanied by development of scientific research devoted to the skin and also, for about ten years or so, by a rapid growth in the market for "anti-aging" cosmetic products or cosmetic products intended to improve the general condition of the skin.

The present invention falls within this context of the search for new molecules or compositions which, when applied to the skin, produce, by virtue of their own activity, a "plumping" effect on the skin and/or "densifying" effect on the skin and/or "volumizing" effect on the skin and/or an effect which improves the elasticity of the skin of various parts of the human body, such as the hands, buttocks, face, bust and eyelids.

In mammals, adipose tissue constitutes a layer of storage fat which envelops the body, but the thickness of which differs depending on the area of the body, on age and on sex. In women, adipose tissue represents from 20 to 25% of the total weight, whereas in men, it varies between 15 and 20% of the total weight. Men and women have different sites of location of adipose tissue, this being due mainly to the various hormonal factors synthesized by the human body depending on the sex. Owing to its importance, adipose tissue contributes to the general appearance of the figure and of the face of human beings. Adipose tissue is generally found in the face, the limbs, the abdomen, the hands and the buttocks. In women, adipose tissue is also present in the bust, and more particularly in the breasts. A woman's breast consists of the mammary gland, the connective tissue and the adipose tissue. The adipose tissue represents a large part of the volume of the breasts, and consequently its proportion and its distribution determine breast size and shape. Depending on the stages of life (pregnancy, breastfeeding, youth, pronounced weight loss, disease), the proportion and the distribution of adipose tissue in the breast undergo variations which bring about modifications in breast volume and shape, which can thus lead either to sagging or to firming of the breast. In terms of the face, adipose tissue makes it possible to form the features and expressions of each individual. Too great a weight loss or skin aging can cause a decrease in the proportion of adipose tissue in the face, and lead to a modification of the features and of the expression of individuals.

The skin aging mechanism can be explained in the following way:

The skin is made up of three major tissues with, in order from the outer surface: the epidermis, the dermis and the hypodermis.

The epidermis is essentially composed of keratinocytes. These cells proliferate in the basal stratum and then gradually differentiate to give the various layers of the epidermis while migrating from the bottom to the surface, where they desquamate.

The dermis is a dense and fibroelastic connective tissue, the production and any remodeling of which are essentially carried out by the fibroblasts, and which consists of the extracellular matrix (ECM) composed of fibrous (collagen and elastic) molecules responsible for the esthetic qualities of the skin, and also the ground substance. Collagens represent 98% of the dry weight of the dermis. The ground substance is composed of macromolecules which fill the spaces between the cells and the fibers; of structural glycoproteins, which allow the connection of the cells to the ECM and which are essentially located under the dermal-epidermal junction, and of proteoglycans consisting of glycosaminoglycans (GAGs) which are bonded to a protein (covalent bonding).

The hypodermis constitutes the deep layer of the skin. It is composed of adipose tissue and connective tissue, and it is richly vascularized and innervated. At the interface of the dermis and the underlying mobile structures (muscles, tendons, organs), the hypodermis plays the role of a shock absorber and protects these underlying mobile structures against external mechanical pressures. Owing to the nature of the adipose tissue, the hypodermis also has an important energy, metabolic and thermal role. It stores in particular excess food energy intakes, in the form of triglycerides (TGs), a phenomenon known as lipogenesis, so as to subsequently be able to redistribute them as required by the human body, a phenomenon known as lipolysis. The main players in this adipose tissue are the adipocytes and their precursors, preadipocytes. The adipocyte is in the form of an extendable round cell which has a large lipid vacuole that takes up the entire cytoplasmic space and pushes the nucleus to the cell periphery. The preadipocyte is a small cell of fibroblast morphotype, which does not possess any metabolic activity relating to energy storage. When it is in the presence of appropriate extracellular signals, it begins a process of differentiation in order to acquire the mature adipocyte phenotype. This process, widely described in vitro, takes several weeks and is made possible by the coordinated expression of various transcription factors targeting the genes specific for lipid metabolism (Fève et al. Grégoire et al., 1998). This process is thus commonly described as adipogenesis or adipocyte differentiation or else adipocyte conversion. It has recently been demonstrated that preadipocytes are present in adipose tissue throughout the existence of the human being, representing from 15 to 50% of the cells of this tissue in adults (Yu et al. 2004; Guo et al., 2006). Thus, at any time of life, preadipocytes can differentiate into adipocytes, thus resulting in a renewal of the cells of the adipose tissue or in the expansion of said tissue. However, it would appear that certain periods in human development are essential in increasing the number of adipocytes and, consequently, in the forming of the fat mass. The first year of life and the period of adolescence are in particular two important periods during which adipose tissue appears to be more subject to considerable changes in its constitution (Smith et al., 2006).

Skin aging, and more particularly facial aging, which preoccupies many individuals, is characterized by two tissue phenomena, ptosis and atrophy.

Ptosis is linked to a loss of tonicity of all the components of the skin (tissue, ligaments, muscles). The cutaneous tissue loses its elasticity and develops ptosis with the underlying fat (Dumont et al., 2007). The visual characteristics of this phenomenon are none other than exacerbated visualization of the nasal fold, dropping of the jowls, etc.

Atrophy occurs in a second step and plays a predominant role in the volumetric modifications that occur on the face with aging. It admittedly involves the adipose tissue, but also all the other structural layers (dermis, epidermis, muscle, etc.). This adipose tissue atrophy phenomenon also worsens the ptosis through the creation of a "content-container" imbalance (Dumont et al., 2007). The visible consequences of this phenomenon are the observation of sunken faces, and of a lack of volume and/or of fullness of the skin. The adipose tissue in fact undergoes many physiological and metabolic changes during aging. The adipose tissue atrophy observed can be explained by various phenomena which set in and which affect both the adipocytes and the preadipocytes. In terms of the adipocytes, a decrease in their size is observed, while their number remains constant (I. Karagiannides et al., 2001, 2006). This can be explained by the observation of a decrease both in their ability to accumulate lipids and in their ability to perform lipolysis. The preadipocytes are also affected by the aging process. Indeed, their ability to differentiate into adipocytes and, consequently, the ability of the adipocytes resulting therefrom to accumulate lipids, is decreased (I. Karagiannides et al., 2001, 2006). Furthermore, the adipose tissue, with its high concentrations of cytotoxic free fatty acids, coupled to a large number of macrophages and of pro-inflammatory cytokines, can inflict damage on the quiescent preadipocytes, leading to differentiation into an incomplete adipocyte (Guo et al., 2006; I. Karagiannides et al., 2006). The nonfunctionalized cells thus created have been described by Kirkland (Kirkland et al., 2002) and called MAD (Mesenchymal Adipocyte-like Default) cells. These MAD cells are cells which are smaller and less responsive to insulin than functional adipocytes. They are also characterized by a reduced fatty acid metabolization capacity and produce larger amounts of TNFα cytokine. The production of this TNFα cytokine in large amounts prevents the differentiation of the adjacent preadipocytes and can transform them, in turn, into MAD cells. The loss of elasticity of human skin, more particularly the loss of elasticity of certain parts of the human body, such as the breasts, the face, the cheeks, the buttocks and the eyelids, can be explained by the fact that the dermis contains elastic fibers and collagen fibers, which determine mainly the viscoelastic properties of human skin, and that the hypodermis, the deepest layer of human skin, also acts on these properties. Indeed, the hypodermal tissue compresses the dermis in a varying manner, depending on its thickness; thus, an increase in the thickness of a hypodermis can lead to a modification of the biomechanical properties of the skin and in particular an improvement in its elasticity. In order to meet the expectations of individuals wishing to improve the appearance of their figure, or of their bust, or of their hands, or of their face, solutions of surgical nature exist. One of these techniques is known as lipo-filling and consists in removing the adipose tissue from a part of the human body of an individual in order to implant it under the skin of another site of the body of the same individual that it is desired to correct by increasing the volume. However, these surgical techniques have the drawback of being invasive and expensive and of leaving scars on the body that are visible for a long period of time. Many "anti-aging" or "anti-wrinkle" active ingredients also exist which can be administered to human beings in various ways. Several of these "active" ingredients are capable of regulating the phenotype and/or the properties of normal human fibroblasts. For example, many cosmetic active ingredients stimulate the fibroblastic production of collagen present in the dermis. Thus, among the N-acyl derivatives of amino acids used in cosmetic applications, some exhibit anti-aging biological properties, such as dipalmitoyl hydroxyproline (Sepilift™ DPHP). Other active ingredients focus more on protecting the epidermis, with free-radical-scavenging effects, or effects on maintaining and/or improving the functions of the epidermis according to differentiation and/or immunity mechanisms. On the other hand, few anti-aging active ingredients are known for their ability to act on the adipose tissue present in the hypodermis by promoting the metabolism of the cells making up said hypodermis, in order to give the skin volume again, and/or to "plump" it and/or to give it elasticity again. Among these, mention may be made of the phytosterol sapogenin triterpenoid (described in patent application WO2008/015639 A2) or extracts based on *Commiphora mukul*, which act on cells not altered by aging. International publication WO 90/14429 A1 describes N-hexadecanoyl isoleucine and teaches the use thereof for preparing detergent compositions. The publication JP 2003-096039 describes a method for preparing N-acyl amino acid salts, and also their surface properties and their fungistatic action. This publication describes particularly the sodium, potassium, triethylamine and arginine salts of N-hexadecanoyl isoleucine. International publication WO 98/09611 describes the use of N-acyl amino acids as regulators of skin physiology, and more particularly as an agent for stimulating cell metabolism and restructuring the skin barrier. The publication entitled "Lipoaminoacides et cosmétologie" ["Lipoamino acids and cosmetology"] by J. Morelle (Parfums cosmétiques savons de France, Paris, vol. 3, No. 2, 1 Feb. 1973) describes the use of N-acyl amino acids as stimulators of the cell development process for their antiseborrheic, antifungal and antibacterial properties. The publication FR 2 873 575 A1 describes cosmetic compositions comprising N-acyl amino acids used for providing an anti-aging effect on the skin which can denote a skin elasticity-restoring effect by improving connective tissues.

To our knowledge, no N-acyl amino acid has been described as being capable of regulating the activity of the cells present in the adipose tissue of the hypodermis, by improving adipocyte differentiation and/or by inducing an increase in the overall surface area of the adipocytes and/or by restoring the adipocyte phenotype. Neither has any N-acyl amino acid been described as being capable of causing an increase in the volume of the adipose tissue of the hypodermis on any area of the human body, thus being reflected by a measurable increase in the volume of said area, or as being capable of causing an increase in the density and in the thickness of the adipose tissue of the hypodermis on any area of the human body, thus being reflected by a visible increase in the volume of said area.

Consequently, according to a first aspect, the subject of the invention is the cosmetic use of N-hexadecanoyl isoleucine of formula (I):

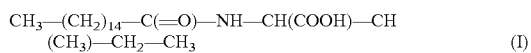  (I)

as a "volumizing" agent and/or as a "plumping" agent for human skin.

The expression "cosmetic use of N-hexadecanoyl isoleucine of formula (I)" denotes in particular a use intended to beautify and/or to improve the appearance of the human body.

The expression "N-hexadecanoyl isoleucine of formula (I) as a "volumizing" agent for human skin" is intended to mean any effect of the N-hexadecanoyl isoleucine of formula (I) which leads to an increase in the volume of the adipose tissue of the hypodermis on any area of the human body, thus being reflected by a measurable increase in the volume of said area. The "volumizing" effect can be analyzed, measured and quantified by ultrasound or by implementing techniques suitable for the area of the human body for which it is desired to demonstrate this effect. For example, in order to demonstrate the "volumizing" effect on women's breasts, it will be possible to measure the change in the bust measurement.

The expression "N-hexadecanoyl isoleucine of formula (I) as a "plumping" agent for human skin" is intended to mean any effect of the N-hexadecanoyl isoleucine of formula (I) which leads to an increase in the density and in the thickness of the adipose tissue of the hypodermis on any area of the human body, thus being reflected by a visible increase in the volume of said area. The "plumping" or "redensifying" effect on the adipose tissue can be analyzed by the fringe projection technique or by ultrasound.

In the context of the demonstration of the "volumizing" effect and of the "plumping" effect of the N-hexadecanoyl isoleucine of formula (I), the applicant has demonstrated the action of the N-hexadecanoyl isoleucine of formula (I) for regulating the activity of the cells present in the adipose tissue of the hypodermis of human skin. In the expression "for regulating the activity of the cells present in the adipose tissue of the hypodermis of human skin", it is more particularly denoted that the N-hexadecanoyl isoleucine of formula (I) has one or other, several or all of the following properties:
- it improves the differentiation of the adipocytes present in the adipose tissue of the hypodermis of human skin;
- it increases the overall surface area of the adipocytes present in the adipose tissue of the hypodermis of human skin;
- it restores the adipocyte phenotype in the adipose tissue of the hypodermis of human skin and, consequently, prevents the generation of altered cells in the adipose tissue of the hypodermis of human skin.

The N-hexadecanoyl isoleucine of formula (I) can be in free acid form or in partially or totally salified form. When the N-hexadecanoyl isoleucine is in salified form, this involves in particular alkali metal salts such as the sodium, potassium or lithium salts, alkaline-earth metal salts such as the calcium, magnesium or strontium salts; an ammonium salt or amino alcohol salts, for instance the (2-hydroxyethyl) ammonium salt. It may also involve metal salts such as zinc or manganese divalent salts, or iron, lanthanum, cerium or aluminum trivalent salts. Generally, the degree of salification of the N-hexadecanoyl isoleucine of formula (I) will among other things depend on its pKA and on the salt concentration of the composition into which it is incorporated. In the following description, the term "N-hexadecanoyl isoleucine of formula (I)" is intended to mean the N-hexadecanoyl isoleucine of formula (I) in free or partially or totally salified form.

The N-hexadecanoyl isoleucine of formula (I) is generally obtained by N-acylation of isoleucine or of salts thereof using as acylating agent an activated derivative of hexadecanoic acid of formula:

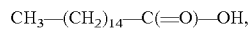

such as a symmetric anhydride of this acid, a methyl ester of this acid, or an acid halide such as the acid chloride or the acid bromide. The acylation reaction is known to those skilled in the art. It is described, for example, in the patent application published under number WO 98/09611.

According to a more particular aspect, the subject of the invention is the cosmetic use of N-hexadecanoyl isoleucine of formula (I), characterized in that the N-hexadecanoyl isoleucine of formula (I) also promotes the expansion of the adipose tissue of the hypodermis of human skin.

The expression "promoting the expansion of the adipose tissue of the hypodermis of human skin" is intended to denote any increase in the mass and/or in the volume and/or in the thickness of the adipose tissue of the hypodermis of human skin.

According to a more particular aspect, the subject of the invention is the cosmetic use of N-hexadecanoyl isoleucine of formula (I), characterized in that the N-hexadecanoyl isoleucine of formula (I) also stimulates an increase in the elasticity of and/or a "volumizing" effect and/or a "plumping" effect on human skin.

Human skin has rheological properties evaluated according to two parameters:
- an elastic parameter,
- a tension parameter which varies according to the various areas of the human body.

In the context of the present invention, the expression "N-hexadecanoyl isoleucine of formula (I) stimulates an increase in the elasticity" of human skin is intended to mean any effect of the N-hexadecanoyl isoleucine of formula (I) which leads to a decrease in the elastic parameter in ballistometry of human skin, thus corresponding to an increase in the elasticity of human skin.

The biomechanical properties can be analyzed, measured and quantified by techniques based on the study of the change in these parameters, for instance techniques involving the use of a "Cutometer™", or of a "Dermal Torque Meter™" or of a "Ballistometer™".

According to a second aspect, the subject of the invention is a cosmetic treatment process for the human body for obtaining a "volumizing" and/or "plumping" effect on the skin of a part of the human body chosen from the breasts, the face, the cheeks, the buttocks and the eyelids, characterized in that it consists in applying, to said part, a cosmetic composition comprising an effective amount of N-hexadecanoyl isoleucine of formula (I).

The expression "effective amount of N-hexadecanoyl isoleucine of formula (I) to be applied to the skin of a part of the human body chosen from the breasts, the face, the cheeks, the buttocks and the eyelids for obtaining a "volumizing" and/or "plumping" effect on the skin of said part" is intended to mean the amount of between 0.000001% and 0.5% by weight, more particularly between 0.00001% and 0.05% by weight, and even more particularly between 0.0001% and 0.005% by weight of N-hexadecanoyl isoleucine of formula (I).

According to a more particular aspect, the subject of the invention is a cosmetic treatment process for the human body, as defined above, characterized in that it also makes it possible to promote the expansion of the adipose tissue of the hypodermis of human skin.

According to an even more particular aspect, the subject of the invention is a cosmetic treatment process for the human body, as defined above, characterized in that the application of the effective amount of N-hexadecanoyl isoleucine of formula (I) is carried out on the breasts and/or on the face and/or on the cheeks and/or on the buttocks and/or on the eyelids for obtaining an increase in the elasticity of the skin and/or a volumizing effect and/or a plumping effect.

In the cosmetic treatment process for the human body which is the subject of the present invention, the N-hexadecanoyl isoleucine of formula (I) is generally included in a composition comprising cosmetically acceptable ingredients.

The expression "cosmetically acceptable" used in the definition of the ingredients combined with the N-hexadecanoyl isoleucine of formula (I) in the compositions used in the cosmetic treatment process which is the subject of the present invention, signifies, according to European Economic Community Council directive No. 76/768/EEC of Jul. 27, 1976, amended by directive No. 93/35/EEC of Jun. 14, 1993, that said composition comprises any substance or preparation intended to be brought into contact with the various parts of the human body (epidermis, body hair and head hair system, nails, lips and genital organs) or with the teeth and the oral mucosae for the purpose, exclusively and principally, of cleaning them, of fragrancing them, of modifying the appearance thereof and/or of correcting the body odors thereof and/or of protecting them or of maintaining them in good condition.

The compositions comprising the N-hexadecanoyl isoleucine of formula (I) used in the cosmetic treatment process for the human body which is the subject of the present invention are generally in the form of dilute aqueous or aqueous-alcoholic solutions, in the form of simple or multiple emulsions, such as water-in-oil (W/O), oil-in-water (O/W) or water-in-oil-in-water (W/O/W) emulsions, in which the oil is of plant or mineral nature, or in the form of a powder. They can also be dispersed or impregnated on textile material or on nonwoven materials, whether this involves wipes, paper towels or clothing.

The compositions comprising the N-hexadecanoyl isoleucine of formula (I) used in the cosmetic treatment process for the human body which is the subject of the present invention are administered more particular via the direct or indirect topical route, by means of a textile support or of nonwoven materials as described above.

In the compositions comprising the N-hexadecanoyl isoleucine of formula (I) used in the cosmetic treatment process for the human body which is the subject of the present invention as defined above, the N-hexadecanoyl isoleucine of formula (I) is generally used in an amount of between 0.01% and 10% by weight for 100% of the weight of said composition, more particularly between 0.1% and 5% by weight, and quite particularly between 1% and 5% by weight.

Generally, the N-hexadecanoyl isoleucine of formula (I) is combined with many types of adjuvants or of active ingredients used in the cosmetic compositions employed in the cosmetic treatment process for the human body which is the subject of the present invention, whether they are fatty substances, organic solvents, thickeners, gelling agents, softeners, detergent surfactants, overfatting agents, thickening and/or gelling surfactants, antioxidants, opacifiers, stabilizers, foaming agents, fragrances, emulsifying surfactants, hydrotropic agents, plasticizers, overfatting agents, texturing agents, pigments, sequestering agents, chelating agents, preservatives, chemical screening agents or mineral screening agents, essential oils, dyestuffs, pigments, hydrophilic or lipophilic active agents, humectants, for example glycerol, preservatives, dyes, fragrances, cosmetic active agents, mineral or organic sunscreens, mineral fillers such as iron oxides, titanium oxides and talc, synthetic fillers such as nylons and crosslinked or noncrosslinked poly(methyl methacrylate)s, silicone elastomers, sericites or plant extracts or else lipid vesicles or any other ingredient normally used in the cosmetics industry.

As examples of oils that can be combined with the N-hexadecanoyl isoleucine of formula (I) in the cosmetic compositions used in the cosmetic treatment process for the human body which is the subject of the present invention, mention may be made of mineral oils such as liquid paraffin, liquid petroleum jelly, isoparaffins or white mineral oils, oils of animal origin, such as squalene or squalane, plant oils, such as sweet almond oil, coconut oil, castor oil, jojoba oil, olive oil, rapeseed oil, groundnut oil, sunflower oil, wheat germ oil, corn germ oil, soya oil, cottonseed oil, alfalfa oil, poppyseed oil, pumpkin oil, evening primrose oil, millet oil, barley oil, rye oil, safflower oil, candlenut oil, passionflower oil, hazelnut oil, palm oil, Shea butter, apricot kernel oil, beauty leaf oil, sysymbrium oil, avocado oil, calendula oil; ethoxylated plant oils; synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, for instance glyceryl triheptanoate, alkyl benzoates, poly-alpha-olefins, polyolefins such as polyisobutene, synthetic isoalkanes, for instance isohexadecane or isododecane, perfluoro oils and silicone oils. Among the latter, mention may more particularly be made of dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups.

As other fat that can be combined with the N-hexadecanoyl isoleucine of formula (I) in the cosmetic compositions used in the cosmetic treatment process for the human body which is the subject of the present invention, mention may be made of fatty alcohols or fatty acids.

As examples of waxes that can be combined with the N-hexadecanoyl isoleucine of formula (I) in the cosmetic compositions used in the cosmetic treatment process for the human body which is the subject of the present invention, mention may be made, for example, of beeswax; carnauba wax; candelilla wax; ouricury wax; Japan wax; cork fiber wax or sugarcane wax; paraffin waxes; lignite waxes; microcrystalline waxes; lanolin wax; ozokerite; polyethylene wax; hydrogenated oils; silicone waxes; plant waxes; fatty alcohols and fatty acids which are solid at ambient temperature; and glycerides which are solid at ambient temperature.

As examples of thickening and/or emulsifying polymers that can be combined with the N-hexadecanoyl isoleucine of formula (I) in the cosmetic compositions used in the cosmetic treatment process for the human body which is the subject of the present invention, mention may be made, for example, of homopolymers or copolymers of acrylic acid or of acrylic acid derivatives, acrylamide homopolymers or copolymers, homopolymers or copolymers of acrylamide derivatives, homopolymers or copolymers of acrylamidomethylpropanesulfonic acid, of vinyl monomer and of trimethylaminoethyl acrylate chloride, hydrocolloids of plant or biosynthetic origin, for example xanthan gum, karaya gum, carrageenates, alginates; silicates; cellulose and derivatives thereof; starch and hydrophilic derivatives thereof; polyurethanes.

Among the polymers of polyelectrolyte type that can be combined with the N-hexadecanoyl isoleucine of formula (I), there are, for example, copolymers of acrylic acid and of 2-methyl-[(1-oxo-2-propenyl)amino]-1-propane-sulfonic acid (AMPS), copolymers of acrylamide and of 2-methyl-[(1-oxo-2-propenyl)amino]-1-propanesulfonic acid, copolymers of 2-methyl-[(1-oxo-2-propenyl)amino]-1-propanesulfonic acid and of (2-hydroxyethyl) acrylate, 2-methyl-[(1-oxo-2-propenyl)amino]-1-propane-sulfonic acid homopolymer, acrylic acid homopolymer, copolymers of acryloylethyltrimethylammonium chloride and of acrylamide, copolymers of AMPS and of vinylpyrrolidone, copolymers of acrylic acid and of alkyl acrylates of which the carbon-based chain comprises between ten and thirty carbon atoms, and copolymers of AMPS and of alkyl acrylates of which the carbon-based chain comprises between ten and thirty carbon atoms. Such polymers are sold respectively under the names Simulgel™ EG, Sepigel™ 305, Simulgel™ NS, Simulgel™ 800 and Simulgel™ A by the applicant.

As examples of emulsifiers that can be combined with the N-hexadecanoyl isoleucine of formula (I) in the cosmetic compositions used in the cosmetic treatment process for the human body which is the subject of the present invention, mention may be made, for example, of fatty acids, ethoxylated fatty acids, fatty acid esters of sorbitol, ethoxylated fatty acid esters, polysorbates, polyglycerol esters, ethoxylated fatty alcohols, sucrose esters, alkylpolyglycosides, sulfated and phosphated fatty alcohols or the mixtures of alkylpolyglycosides and of fatty alcohols described in French patent applications 2 668 080, 2 734 496, 2 756 195, 2 762 317, 2 784 680, 2 784 904, 2 791 565, 2 790 977, 2 807 435 and 2 804 432.

As examples of active ingredients that can be combined with the N-hexadecanoyl isoleucine of formula (I) in the cosmetic compositions used in the cosmetic treatment process for the human body which is the subject of the present invention, mention may be made of compounds which have a lightening or depigmenting action, for instance arbutin, kojic acid, hydroquinone, ellagic acid, vitamin C, magnesium ascorbyl phosphate, polyphenol extracts, glycosylated polyphenol derivatives such as rosmarinyl glucoside, grape extracts, pine extracts, wine extracts, olive extracts, pond extracts, N-acylated proteins, N-acylated peptides, N-acylated amino acids, partial hydrolysates of N-acylated proteins, amino acids, peptides, total protein hydrolysates, partial protein hydrolysates, polyols (for example, glycerol or butylene glycol), urea, pyrrolidonecarboxylic acid or the derivatives of this acid, glycyrrhetinic acid, alpha-bisabolol, sugars or sugar derivatives, polysaccharides or derivatives thereof, hydroxy acids, for example lactic acid, vitamins, vitamin derivatives, for instance retinol, vitamin E and its derivatives, minerals, enzymes, coenzymes, for instance coenzyme Q10, hormones or hormone-like substances, soya extracts, for example Raffermine™, wheat extracts, for example Tensine™ or Gliadine™, plant extracts, such as tannin-rich extracts, isoflavone-rich extracts or terpene-rich extracts, fresh water or saltwater algal extracts, essential waxes, bacterial extracts, minerals, lipids in general, lipids such as ceramides or phospholipids, active agents which have a slimming action, for instance caffeine or its derivatives, for instance the quinoa extract sold under the name Adipoless™, for instance the hemlock spruce extract sold under the name Sereniks™ 207, for instance the composition comprising lauroyl proline sold under the name Adiposlim™, active agents which have an antimicrobial activity or a purifying action with respect to oily skin, such as Lipacide™ PVB, active agents which have an energizing or stimulating property, for instance Sepitonic™ M3 or Physiogenyl™, panthenol and its derivatives, for instance Sepicap™ MP, anti-aging active agents, for instance Sepilift™ DPHP, Lipacide™ PVB, Sepivinol™, or Sepivital™, moisturizing active agents, for instance Sepicalm™ S, Sepicalm™ VG and Sepilift™ DPHP, "anti-photoaging" anti-aging active agents; active agents which protect the integrity of the dermal-epidermal junction, active agents which increase the synthesis of extracellular matrix components, active agents which have a slimming, firming or draining activity, for instance caffeine, theophylline, cAMP, green tea, sage, *ginkgo biloba*, ivy, horse chestnut, bamboo, ruscus, butcher's broom, *Centella asiatica*, heather, meadowsweet, fucus, rosemary or willow, active agents which create a feeling of "heating" on the skin, for instance activators of the capillary microcirculation (for example nicotinates) or products which create a feeling of "freshness" on the skin (for example, menthol and derivatives).

As examples of texturing agents that can be combined with the N-hexadecanoyl isoleucine of formula (I) in the cosmetic compositions used in the cosmetic treatment process for the human body which is the subject of the present invention, mention may be made of N-acylated derivatives of amino acids, for instance the lauroyllysine sold under the name Aminohope™ LL by the company Ajinomoto, the octenyl starch succinate sold under the name Dryflo™ by the company National Starch, the myristyl polyglucoside sold by SEPPIC under the name Montanov™ 14, cellulose fibers, cotton fibers, chitosan fibers, talc, sericite and mica.

As examples of opacifiers and/or pearlescent agents that can be combined with the N-hexadecanoyl isoleucine of formula (I) in the cosmetic compositions used in the cosmetic treatment process for the human body which is the subject of the present invention, mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate and fatty alcohols.

As examples of thickening and/or gelling surfactants that can be combined with the N-hexadecanoyl isoleucine of formula (I) in the cosmetic compositions used in the cosmetic treatment process for the human body which is the subject of the present invention, mention may be made of:
  optionally alkoxylated alkylpolyglycoside fatty esters, and quite particularly ethoxylated methylpolyglucoside esters, such as the PEG 120 methyl glucose trioleate and the PEG 120 methyl glucose dioleate sold respectively under the names Glucamate™ LT and Glumate™ DOE120;
  alkoxylated fatty esters, such as the PEG 150 pentaerythrityl tetrastearate sold under the name Crothix™ DS53 or the PEG 55 propylene glycol oleate sold under the name Antil™ 141;
  fatty-chain polyalkylene glycol carbamates, such as the PPG 14 laureth isophoryl dicarbamate sold under the name Elfacos™ T211 or the PPG 14 palmeth 60 hexyl dicarbamate sold under the name Elfacos™ GT2125.

As examples of sunscreens that can be combined with the N-hexadecanoyl isoleucine of formula (I) in the cosmetic compositions used in the cosmetic treatment process for the human body which is the subject of the present invention, mention may be made of those which appear in cosmetics directive 76/768/EEC amended, annex VII.

The following experimental studies illustrate the invention without, however, limiting it.

1—In Vitro Studies

The in vitro studies demonstrate that the N-hexadecanoyl isoleucine of formula (I) regulates the activity of hypodermal adipose tissue cells by making it possible to stimulate the differentiation of normal human preadipocytes in a model reproducing conditions of adipogenic stimulation insufficiency, by making it possible to stimulate the increase in adipocyte surface area, and by making it possible to restore the adipocyte phenotype of "young" normal human preadipocytes in a model reproducing aging conditions.

1.1—Demonstration of the Stimulatory Effectiveness of N-Hexadecanoyl Isoleucine on the Differentiation of Normal Human Preadipocytes in an In Vitro Model Reproducing Conditions of Adipogenic Stimulation Insufficiency, and on the Stimulatory Effectiveness of N-Hexadecanoyl Isoleucine on the Increase in Adipocyte Surface Area Protocol Normal human preadipocytes resulting from abdominal surgical waste from a 38-year-old female donor were cultured in monolayer until confluence in the presence of a culture medium comprising PBM-2 (Preadipocyte Basal Medium-2) supplied by the company Lonza, an amount of 10% by volume of FBS (Fetal Bovine Serum) for 100% of the volume of the culture medium, L-glutamine and gentamicin.

Their differentiation into adipocytes was induced by adding a "depleted" differentiation medium comprising a mixture of insulin, dexamethasone, IBMX (isobutyl methyl xanthine) and indomethacin, and used at a dilution rate of $1/10^{th}$ with respect to a "standard" differentiation medium. This phase of differentiation by adding a "depleted" differentiation medium is carried out in the presence of the products tested in the context of the present demonstration, namely N-hexadecanoyl isoleucine, hexadecanoic acid, isoleucine, and a mixture of hexadecanoic acid and of isoleucine in a hexadecanoic acid/isoleucine ratio by weight of 65/35, and also in the absence of products so as to obtain a "control differentiated in depleted medium".

A differentiation phase is also carried out on human preadipocytes as described above and cultured in monolayers as described above, but in the presence of a "standard" differentiation medium, namely a nondiluted mixture of insulin, dexamethasone, IBMX (IsoButyl Methyl Xanthine) and indomethacin, so as to obtain a "control differentiated in standard medium".

Once the maturity of the preadipocytes was reached, namely after 15 days following the induction described above, the cultures were rinsed with a PBS (Phosphate Buffered Saline) buffer and the intracytoplasmic lipid vesicles were labeled using a specific viable fluorescent probe, Bodipy (500 μg/ml). The nuclei of the differentiated preadipocytes were also labeled using a Hoechst reagent (bisbenzimide), which is also fluorescent, at a concentration of 2 μg/ml, sold by the company Sigma.

Three photographs per well were taken using a Zeiss Axiovert™ 25 inverted epifluorescence microscope fitted with an ×20 objective.

Results

For each test of products tested, including controls, the images obtained with the inverted epifluorescence microscope are analyzed using the Lucia software, allowing quantification of the Bodipy fluorescent label, in order to carry out:
 a measurement of the lipid droplet surface area (Sd),
 a measurement of the number of differentiated cells (Nc), and
 a measurement of the number of total cell nuclei (Nnc).

For each test, the level of adipocyte differentiation (D) is then calculated by relating the lipid droplet surface area to the number of total nuclei according to the following formula: (D)=(lipid droplet surface area)/(number of total cell nuclei).

The following will thus be calculated:
 the level of adipocyte differentiation of the control differentiated in depleted medium (subsequently denoted Ddm);
 the level of adipocyte differentiation of the control differentiated in standard or complete medium (subsequently denoted Dcm);
 the level of adipocyte differentiation of the products tested (N-hexadecanoyl isoleucine, hexadecanoic acid, isoleucine, hexadecanoic acid/isoleucine mixture in a ratio by weight of 65/35) (subsequently denoted Dpt).

For each product tested, the following are then calculated:

a) the percentage restoration of adipocyte differentiation (subsequently denoted RAD) according to the following formula:

$$RAD=[(Dpt-Ddm)/(Dcm-Ddm)]\times 100$$

b) the adipocyte surface area (AS) according to the following formula:

$$(AS)=[(\text{lipid droplet surface area } Sd)/(\text{number of differentiated cells } Nc)]\times 100$$

c) the percentage increase in adipocyte surface area (subsequently denoted IAS) relative to the control treated with depleted medium according to the formula:

$$IAS=[\text{adipocyte surface area of the product } (ASpt)/\text{adipocyte surface area of the control treated with the depleted medium } (ASdm)]\times 100.$$

A statistical analysis is then carried out on the data (D) and (AS) using a two-sided Student's test assuming unequal variances. Thus, the population of each of the experimental conditions tested for the parameters (D) and (AS) is compared with the population of the condition of differentiation in the presence of the depleted differentiation medium. An error threshold (p) is set at 5%. If $p \leq 0.05$, the two populations studied are considered to be significantly different, and the experimental condition studied then has an effect compared with the condition of differentiation in depleted medium. If $p > 0.05$, the two populations are considered not to show any differences and, consequently, the experimental condition studied does not have an effect compared with the condition of differentiation in depleted medium.

The results obtained are reported in Table 1 below:

TABLE 1

| Products tested | RAD | IAS |
| --- | --- | --- |
| Control differentiated in depleted medium | 0% | 100% |
| Control differentiated in standard medium | 100%* | 194%* |

TABLE 1-continued

| Products tested | RAD | IAS |
|---|---|---|
| N-hexadecanoyl isoleucine (5 µg/ml on a dry extract basis) | 63%* | 215%* |
| N-hexadecanoyl isoleucine (10 µg/ml on a dry extract basis) | 85%* | 214%* |
| Hexadecanoic acid (3.3 µg/ml) | <10% | 41%* |
| Hexadecanoic acid (6.5 µg/ml) | <10% | 62% |
| Isoleucine (1.7 µg/ml on a dry extract basis) | <10% | 57% |
| Isoleucine (3.3 µg/ml on a dry extract basis) | <10% | 117% |
| Hexadecanoic acid/isoleucine (65/35) (5 µg/ml on a dry extract basis) | <10% | 88% |
| Hexadecanoic acid/isoleucine (65/35) (10 µg/ml on a dry extract basis) | <10% | 49% |

*Result statistically significant compared with the control differentiated in depleted medium (two-sided Student's test assuming unequal variances) with p ≤ 0.05.

The tests carried out according to the protocol described above and included in Table 1 show that the N-hexadecanoyl isoleucine allows an RAD of 63% for a dose of 5 µg/ml, on a dry extract basis, of N-hexadecanoyl isoleucine, and an RAD of 85% for a dose of 10 µg/ml, on a dry extract basis.

When hexadecanoic acid is used at doses of 3.3 µg/ml on a dry extract basis and 6.5 µg/ml on a dry extract basis, and when isoleucine is used at doses of 1.7 µg/ml on a dry extract basis and 3.3 µg/ml on a dry extract basis, the RAD is less than 10% and considered to be nonsignificant. The same is true for the tests with a mixture of hexadecanoic acid and isoleucine in a hexadecanoic acid/isoleucine proportion by weight of 65/35, at doses of 5 µg/ml on a dry extract basis and 10 µg/ml on a dry extract basis.

These results therefore show that the N-acylated structure of N-hexadecanoyl isoleucine allows an effective RAD.

The tests also show that N-hexadecanoyl isoleucine makes it possible to obtain a level of increase of the adipocyte surface area of 215% for a dose of 5 µg/ml on a dry extract basis, and of 214% for a dose of 10 µg/ml on a dry extract basis, compared with 194% for the control differentiated in standard medium. Furthermore, when hexadecanoic acid is used at doses of 3.3 µg/ml on a dry extract basis and 6.5 µg/ml on a dry extract basis, and when isoleucine is used at doses of 1.7 µg/ml on a dry extract basis and 3.3 µg/ml on a dry extract basis, in tests carried out according to the protocol described above, the IAS levels obtained are much lower than that obtained for the control differentiated in standard medium, and in most cases, they are also less than the IAS level obtained for the control differentiated in depleted medium. The same observation is made for the tests carried out with a mixture of hexadecanoic acid and isoleucine in a hexadecanoic acid/isoleucine proportion by weight of 65/35, at doses of 5 µg/ml on a dry extract basis and 10 µg/ml on a dry extract basis.

These results therefore show that the N-acylated structure of the N-hexadecanoyl isoleucine allows an effective IAS.

1.2—Demonstration of the Adipocyte-Phenotype-Restoring Effect with N-Hexadecanoyl Isoleucine Using Normal Human Preadipocytes in an In Vitro Model Reproducing Aging Conditions The in vitro model used consists of an accelerated aging of normal human preadipocytes by successive "passages" in order to generate cells exhibiting a phenotype and the characteristics of MAD cells after differentiation. The term "passage" or "subculturing" or "amplification" denotes here the operation, known to those skilled in the art, consisting in amplifying the cells in question successively by means of culture cycles. Thus, the term "preadipocytes of passage R0" denotes the preadipocytes which have undergone no passage operation as defined above. The term "preadipocytes of passage R1" denotes the preadipocytes which have undergone a single passage operation as defined above. The term "preadipocytes of passage R7" denotes the preadipocytes which have undergone 7 successive passage operations under identical operating conditions. Consequently, the preadipocytes of passage R1 will be considered to be representative of preadipocytes of a "young" individual since they do not exhibit any morphological and phenotypic alterations owing to the successive passage steps. Furthermore, the preadipocytes of passage R7 will be considered to be representative of an artificially aged individual since they exhibit morphological and phenotypic alterations owing to the successive passage steps. Three different protocols were carried out in order to demonstrate the effectiveness of the N-hexadecanoyl isoleucine in restoring the phenotype of differentiated and artificially aged preadipocytes.

Protocol 1 a)—Preparation of the "Young" Control i) Human preadipocytes of passage R1 were cultured in monolayer for 5 days until confluence. Their differentiation into adipocytes was induced by adding a standard differentiation mixture comprising a mixture of insulin, dexamethasone, IBMX (Isobutyl methyl xanthine) and indomethacin.

ii) After a period of 15 days following the induction step described above, the cultures prepared are rinsed with a PBS (phosphate buffered saline) buffer and then fixed using a solution comprising, for 100% of the weight of said solution, 4% by weight of formaldehyde and 0.1% by weight of Triton X-100, which is a synthetic detergent commonly used in biology.

iii) Labeling of the intracytoplasmic lipid vesicles of the cell cultures previously prepared is then carried out using an amount of 0.2% by mass of the Oil-Red-O label sold by the company Sigma.

iv) The cell monolayers containing the lipid vesicles of the cell cultures previously described and labeled as indicated above are then lysed with dimethyl sulfoxide (or DMSO).

v) The amount of labeling of the lipid vesicles of the labeled and lysed cell cultures as prepared at the end of step iv) of the present protocol is then estimated by reading the optical density (OD) of these lysates using a spectrophotometer at a wavelength of 540 nm.

The optical density thus measured for the young control is denoted "$OD_{R1}$".

b)—Preparation of the "Aged" Control

The protocol steps i) to v) described in section a) are applied to human preadipocytes of passage R7, so as to obtain an optical density for the "aged" control, denoted "$OD_{R7}$".

c)—Evaluation of the Effect of the N-hexadecanoyl Isoleucine on Human Preadipocytes of Passage R7

Human preadipocytes of passage R7 were cultured in monolayers for 5 days until confluence. Their differentiation into adipocytes is induced by adding a standard differentiation mixture comprising a mixture of insulin, dexamethasone, IBMX (Isobutyl methyl xanthine) and indomethacin, in the presence of N-hexadecanoyl isoleucine. Steps ii) to v) as described in section a) are then carried out, so as to obtain an optical density for the N-hexadecanoyl isoleucine denoted "$OD_{HIL}$".

d—Calculation of the Degree of Phenotype Restoration

The measurement of the various optical densities makes it possible to calculate a phenotype restoration rate (hereinafter denoted PRR) for N-hexadecanoyl isoleucine, according to the following formula:

$$PRR\ (\%)=[(OD_{HIL}-OD_{R7})/(OD_{R1}-OD_{R7})]\times 100$$

A statistical analysis is then carried out on the optical density data using a two-sided Student's test assuming unequal variances. Thus, the population of each of the experimental conditions tested is compared with the population of the R7 preadipocyte differentiation condition. An error threshold (p) is set at 5%. If p is less than or equal to 0.05, the two populations studied are considered to be significantly different and, consequently, the experimental condition studied is considered to have an effect compared with the R7 preadipocyte differentiation condition. If p is strictly greater than 0.05, the two populations are considered not to show any difference and, consequently, the experimental condition studied is considered not to have any effect compared with the R7 preadipocyte differentiation condition.

The PRRs obtained for various concentrations of N-hexadecanoyl isoleucine are reported in Table 2 below.

TABLE 2

| Products tested | PRR |
| --- | --- |
| Differentiated R7 control | 0% |
| Differentiated R1 control | 100%* |
| N-hexadecanoyl isoleucine (5 µg/ml on a dry extract basis) | 13%* |
| N-hexadecanoyl isoleucine (10 µg/ml on a dry extract basis) | 16%* |

*Results statistically significant compared with the control differentiated in depleted medium (two-sided Student's test assuming unequal variances) with $p \leq 0.05$ Protocol 2

The steps of sections a) and b) of protocol 1 are carried out using human preadipocytes of passage R1 and human preadipocytes of passage R7 so as to obtain a "young" control and an "aged" control and the associated optical densities $OD_{R1}$ and $OD_{R7}$. The effect of the N-hexadecanoyl isoleucine on human preadipocytes of passage R7 is evaluated according to a variant of the procedure of protocol 1, the first step of which consists in culturing the human preadipocytes of passage R7 in a monolayer for 5 days until confluence in the presence of N-hexadecanoyl isoleucine. Their differentiation into adipocytes is induced by adding a standard differentiation mixture comprising a mixture of insulin, dexamethasone, IBMX (Isobutyl methyl xanthine) and indomethacin. Steps ii) to v) as described in section a) of protocol 1 are then carried out, so as to obtain an optical density for the N-hexadecanoyl isoleucine, denoted "$OD_{HIL}$".

Measurement of the various optical densities makes it possible to calculate a phenotype restoration rate (PRR) for the N-hexadecanoyl isoleucine following the implementation of protocol 2, according to the following formula:

$$PRR\ (\%) = [(OD_{HIL} - OD_{R7})/(OD_{R1} - OD_{R7})] \times 100$$

The PRRs obtained for various concentrations of N-hexadecanoyl isoleucine according to protocol 2 are reported in Table 3 below.

TABLE 3

| Products tested | PRR |
| --- | --- |
| Differentiated R7 control | 0% |
| Differentiated R1 control | 100%* |
| N-hexadecanoyl isoleucine (5 µg/ml on a dry extract basis) | 27%* |
| N-hexadecanoyl isoleucine (10 µg/ml on a dry extract basis) | 17%* |

*Results statistically significant compared with the control differentiated in depleted medium (two-sided Student's test assuming unequal variances) with $p \leq 0.05$ Protocol 3

The steps of sections a) and b) of protocol 1 are carried out using human preadipocytes of passage R1 and human preadipocytes of passage R7 so as to obtain a "young" control and an "aged" control and the associated optical densities $OD_{R1}$ and $OD_{R7}$.

The effect of the N-hexadecanoyl isoleucine on human preadipocytes of passage R7 is evaluated according to a variant of the procedure of protocol 2, the first step of which consists in culturing the human preadipocytes of passage R7 in a monolayer for 5 days until confluence in the presence of N-hexadecanoyl isoleucine.

Their differentiation into adipocytes is induced by adding a standard differentiation mixture comprising a mixture of insulin, dexamethasone, IBMX (Isobutyl methyl xanthine) and indomethacin, in the presence of N-hexadecanoyl isoleucine. Steps ii) to v) as described in section a) of protocol 1 are then carried out, so as to obtain an optical density for the N-hexadecanoyl isoleucine, denoted "$OD_{HIL}$".

The measurement of the various optical densities makes it possible to calculate a PRR for the N-hexadecanoyl isoleucine following the implementation of protocol 3, according to the following formula:

$$PRR\ (\%) = [(OD_{HIL} - OD_{R7})/(OD_{R1} - OD_{R7})] \times 100$$

The PRRs obtained for various concentrations of N-hexadecanoyl isoleucine according to protocol 2 are reported in Table 4 below.

TABLE 4

| Products tested | PRR |
| --- | --- |
| Differentiated R7 control | 0% |
| Differentiated R1 control | 100%* |
| N-hexadecanoyl isoleucine (5 µg/ml on a dry extract basis) | 36%* |
| N-hexadecanoyl isoleucine (10 µg/ml on a dry extract basis) | 30%* |

*Results statistically significant compared with the control differentiated in depleted medium (two-sided Student's test assuming unequal variances) with $p \leq 0.05$

CONCLUSION

Irrespective of the protocol implemented, the experimental tests showed a beneficial effect of N-hexadecanoyl isoleucine on the restoration of an adipocyte phenotype under artificial aging conditions. Thus, at a dose of 5 µg/ml, on a dry extract basis, of N-hexadecanoyl isoleucine, this effect was estimated via a phenotype restoration rate of 13% according to protocol 1, via a phenotype restoration rate of 27% according to protocol 2, and via a phenotype restoration rate of 36% according to protocol 3.

2—In Vivo Studies

The following experimental studies illustrate the invention without, however, limiting it.

The in vivo studies demonstrate that the cosmetic use of the N-hexadecanoyl isoleucine of formula (I) and the implementation of a cosmetic treatment process for the human body make it possible to generate "volumizing" and/or "plumping" effects on human skin and/or make it possible to increase the elasticity of the skin.

2.1—Demonstration of the "Volumizing" Effect and of the "Plumping" Effect of a Cosmetic Composition Comprising N-Hexadecanoyl Isoleucine on the Breasts a)—Preparation of an Oil-in-Water (O/W) Emulsion Comprising N-Hexadecanoyl Isoleucine (E1) and of a "Placebo" Oil-in-Water Emulsion (E2)

The emulsions (E1) and (E2) are prepared in the following way:

Step 1): The components of the oily phase and the emulsifying system are successively introduced into a beaker, at a temperature of 80° C., and are subjected to mechanical stirring for a period of 15 minutes, using a stirrer which has an "anchor"-type spindle, at a speed of 80 rpm at a temperature of 80° C., so as to form a homogeneous mixture.

Step 2): The thickening polymer is added to the mixture obtained at the end of step 1) at a temperature of 80° C., as is the aqueous phase, prepared beforehand at ambient temperature by mixing its components. The resulting mixture is then subjected to stirring by means of a rotor-stator emulsifying device, sold by the company Silverson, for a period of 4 minutes at a speed of 3000 rpm at a temperature of 80° C.

Step 3): The mixture obtained at the end of step 2) is cooled over a period of 10 minutes to a temperature of 30° C., and kept stirring throughout the cooling by means of a mechanical stirrer which has an "anchor"-type spindle, at a speed of 80 rpm.

Step 4): The Neolone M×P preservative and the "plaisir" fragrance are then added to the mixture resulting from step 3) at a temperature of 30° C. The pH is then adjusted to a value of 6.5 by adding 50% triethanolamine.

The oil-in-water emulsions (E1) and (E2) have the following compositions (by weight):

TABLE 5

|  | (E1) | (E2) |
|---|---|---|
| Oily phase: | | |
| Liquid paraffin | 8.00% | 8.00% |
| Shea butter | 1.50% | 1.50% |
| DUB DONPG[1] | 5.00% | 5.00% |
| N-hexadecanoyl isoleucine | 1.00% | 0% |
| Thickening polymer | | |
| Simulgel ™ INS 100[2] | 1.00% | 1.00% |
| Aqueous phase | | |
| Water | q.s. 100% | q.s. 100% |
| 50% triethanolamine | q.s. pH = 6.5 | q.s. pH = 6.5 |
| Glycerol | 3.00% | 3.00% |
| Emulsifying system | | |
| Montanov ™ 202[3] | 2.00% | 2.00% |
| Additives | | |
| Neolone ™ MxP[4] | 0.50% | 0.50% |
| Plaisir fragrance | 0.10% | 0.10% |

[1]Neopentyl glycol diethyl hexanoate sold by the company Stéarineries Dubois.
[2]Thickening inverse latex (INCI name: hydroxyethyl acrylate/sodium acryloyldimethyl taurate copolymer and isohexadecane and polysorbate 60) sold by the company SEPPIC.
[3]Self-emulsifiable composition such as those described in EP 0 977 626, based on arachidyl alcohol, on behenyl alcohol and on arachidyl glucosides, sold by the company SEPPIC.
[4]Preservative mixture comprising phenoxyethanol, methyl paraben, propyl paraben and methylisothiazolinone, sold by the company Röhm & Haas.

b)—Evaluation of the "Volumizing" Effect and of the "Plumping" Effect of the Oil-in-Water Emulsions (E1) and (E2) on Breasts These evaluations are carried out by measuring the following criteria:
  measurement of the change in centimeters of the bust measurement (Mb),
  measurement of the change in thickness of the hypodermis of the breast by deep ultrasound;
  measurement of the change in volume of the breasts using the fringe projection technique (Primos Body™).

These evaluations were carried out on a population of 44 female volunteers with an average age of 26, with a bust of cup size A (namely a difference of 2.5 cm between the value of the bust measurement taken at the level of the nipples of the two breasts and the value of the bust measurement taken at the base of the two breasts), which was divided up into two equal groups of 22 volunteers (group I and group II). Each member of group (I) applied emulsion (E1) to both her breasts twice-daily for a period of 28 days, and each member of group (II) applied emulsion (E2) to both her breasts twice-daily for a period of 28 days.

b1)—Evaluation of the "Volumizing" Effect of N-Hexadecanoyl Isoleucine by Measuring the Change in Bust Measurement Protocol Before the start of the application of emulsions (E1) and (E2), and at the end of the period of 28 days of the experiment, the bust measurement (Mb) and the under-bust measurement (Mub) are taken using a tape measure graduated in centimeters.

In parallel, the weight curve for each individual (i) of each group is controlled in order to withdraw, during the interpretation, the measured data relating to individuals having experienced too great a weight loss or weight gain (change in weight of the individual of ±3 kg relative to the weight measured before the start of the study). The number of individuals whose weight change is greater than ±3 kg of the initial weight measured before the start of the experiment is denoted (j). The population N of individuals for each group that will be the population for which the measurements will be interpreted is then calculated according to the formula: N=20−j.

The bust measurement in centimeters is taken on each member (i) of groups (I) and (II), by taking as a base the nipples of the two breasts of each individual. For each member (i) of each group, the bust measurement before the start of the experiment (Mb0i) and the bust measurement at the end of the period of the experiment of 28 days (Mb28i) are thus taken. The change in bust measurement for each member of each group, $\Delta Mbi$, is then calculated according to the following formula:

$$\Delta Mbi = Mb28i - Mb0i$$

The arithmetic mean of the change in bust measurement ($\Delta Mbm$) is then calculated for each group according to the following formula:

$$\Delta Mbm = [\Sigma(\Delta Mbi)]/N$$

The under-bust measurement in centimeters is also taken on each member (i) of groups (I) and (II), by taking as a base the line under the two breasts of each individual. For each member (i) of each group, the under-bust measurement before the start of the experiment (Mub0i) and the under-bust measurement at the end of the period of the experiment of 28 days (Mub28i) are thus taken. The change in bust measurement for each member of each group, $\Delta Mubi$, is then calculated according to the following formula:

$$\Delta Mubi = Mub28i - Mub0i$$

The arithmetic mean of the change in under-bust measurement ($\Delta Mubm$) is then calculated for each group according to the following formula:

$$\Delta Mubm = [\Sigma(\Delta Mubi)]/N$$

Results Obtained

The results of the arithmetic means $\Delta Mbm$ and $\Delta Mubm$ are reported in Table 6 below for groups (I) and (II).

TABLE 6

|  | Group (I) | Group (II) |
|---|---|---|
| $\Delta Mbm$ (cm) | +0.6 | 0 |
| $\Delta Mubm$ (cm) | −0.1 | 0 |

The arithmetic mean of the change in bust measurement ($\Delta Mbm$) of the members of group (I), who applied to their breasts the oil-in-water emulsion (E1) comprising N-hexadecanoyl isoleucine, was measured at +0.6 centimeter, for a change in under-bust measurement (ΔMubm) of −0.1 centimeter.

The arithmetic mean of the change in bust measurement (ΔMbm) of the members of group (II), who applied to their breasts the oil-in-water emulsion (E2) not comprising N-hexadecanoyl isoleucine, was measured at 0 centimeter, for a change in under-bust measurement (ΔMubm) of 0 centimeter.

Interpretation

An increase in bust measurement of which the set of values (Mb28i) is statistically different than the values (Mb0i) is considered to be significant.

An increase in under-bust measurement of which the set of values (Mub28i) is statistically different than the values (Mub0i) is considered to be significant.

The statistical analysis used to evaluate the significance of the increase in bust measurement and of the increase in under-bust measurement is carried out using a two-sided Student's test assuming unequal variances. Thus, the set of values (Mb28i) and the set of values (Mub28i) are respectively compared with the set of values (Mb0i) and the set of values (Mub0i). An error threshold (p) is set at 5%. If p is less than or equal to 0.05, the set of values (Mb28i) and the set of values (Mub28i) are considered to be significantly different, respectively, from the set of values (Mb0i) and the set of values (Mub0i). Consequently, it is possible to conclude that there is a significant increase in the bust measurement and in the under-bust measurement. If p is strictly greater than 0.05, the set of values (Mb28i) and the set of values (Mub28i) will not be considered to be significantly different, respectively, than the set of values (Mb0i) and the set of values (Mub0i). Consequently, it will not be possible to conclude that there is a significant increase in the bust measurement and in the under-bust measurement.

Furthermore, an increase in the bust measurement is considered to be significant when the arithmetic mean (ΔMbm) is greater than or equal to 0.2 cm, provided that the arithmetic mean of the under-bust measurement (ΔMubm) is not greater than ±0.2 cm.

CONCLUSION

It is therefore possible to deduce from the results that the presence of N-hexadecanoyl isoleucine in the oil-in-water emulsion (E1) made it possible to increase, in a significant manner, the mean bust measurement of the members of group (I) and therefore made it possible to give these individuals a "volumizing" effect on their breasts.

b2—Evaluation of the Effect of N-Hexadecanoyl Isoleucine on the Thickness of the Breast Hypodermis Protocol The measurement of the thickness of the breast hypodermis by deep ultrasound was carried out for each member of each group by means of a Sonoline Antares™ ultrasound system sold by the company Siemens, fitted with a probe 6 cm long and 1 cm thick. Before each measurement, a contact gel of the Aquasonic100™ brand is applied to the breast. The measurement is carried out at a frequency of 13 MHz by direct application of the probe to the skin of the breast. The probe is connected to software for processing the data measured and to a Fuji DryPix 7000™ printer.

For each member (i) of each group, this evaluation is carried out by performing the following 3 measurements in 3 different places on the breast:

measurement of the thickness of the hypodermis is performed on the lateral side of the breast (MLi), measurement of the thickness of the hypodermis is performed on the superior-anterior face of the breast (MSAi), and measurement of the thickness of the hypodermis is performed on the inferior-anterior face of the breast (MIAi).

In parallel, the weight curve for each individual (i) of each group is controlled in order to withdraw, during the interpretation, the measured data relating to individuals having undergone too great a weight loss or weight gain (change in weight of the individual of ±3 kg relative to the weight measured before the start of the study). The number of individuals whose weight change is greater than ±3 kg of the initial weight measured before the start of the experiment is denoted (j). The population N of individuals for each group that will be the population for which the measurements will be interpreted is then calculated according to the formula: N=20−j.

For each member (i) of each group, the following are thus measured:

the thickness of the hypodermis on the lateral side of the breast before the start of the experiment (ML0i);

the thickness of the hypodermis on the lateral side of the breast at the end of the period of 28 days of the experiment (ML28i);

the thickness of the hypodermis on the superior-anterior face of the breast before the start of the experiment (MSA0i);

the thickness of the hypodermis on the superior-anterior face of the breast at the end of the period of 28 days of the experiment (MSA28i);

the thickness of the hypodermis on the inferior-anterior face of the breast before the start of the experiment (MIA0i); and the thickness of the hypodermis on the inferior-anterior face of the breast at the end of the period of 28 days of the experiment (MIA28i).

For each member of each group, the following are then calculated:

the change in thickness of the hypodermis on the lateral side of the breast (ΔMLi) according to the formula: ΔMLi=ML28i-ML0i;

the change in the thickness of the hypodermis on the superior-anterior face of the breast (ΔMSAi) according to the formula: ΔMSAi=MSA28i-MSA0i; and the change in the thickness of the hypodermis on the inferior-anterior face of the breast (ΔMIAi) according to the formula: ΔMIAi=MIA28i-MIA0i.

Expression of the Results

On the basis of the measurements taken, indicated above, the following are then calculated for each group:

the mean change in thickness of the hypodermis on the lateral side of the breast (ΔMLm) according to the formula: ΔMLm=[Σ(ΔMLi)]/N;

the mean change in thickness of the hypodermis on the superior-anterior face of the breast (ΔMSAm) according to the formula:

$$\Delta MSAm = [\Sigma(\Delta MSAi)]/N;$$

the mean change in thickness of the hypodermis on the inferior-anterior face of the breast (ΔMIAm) according to the formula:

$$\Delta MIAm = [\Sigma(\Delta MIAi)]/N;$$

the mean thickness of the hypodermis on the lateral side of the breast before the start of the experiment [Mean (ML0)] according to the formula:

$$[\text{Mean}(ML0)] = [\Sigma(ML0i)]/N;$$

the mean thickness of the hypodermis on the superior-anterior face of the breast before the start of the experiment [Mean(MSA0)] according to the formula:

[Mean(MSA0)]=[Σ(MSA0i)]/N;

the mean thickness of the hypodermis on the inferior-anterior face of the breast before the start of the experiment [Mean(MIA0)] according to the formula

[Mean(MIA0)]=[Σ(MIA0i)]/p the level of increase in the thickness of the hypodermis on the lateral side of the breast (IML) according to the formula:

(IML)=[ΔMLm/[Mean(ML0)]]×100 the level of increase in the thickness of the hypodermis on the superior-anterior face of the breast (IMSA) according to the formula:

(IMSA)=[ΔMSAm/[Mean(MSA0)]]×100 the level of increase in the thickness of the hypodermis on the inferior-anterior face of the breast (IMIA) according to the formula (IMIA)=[ΔMIAm/[Mean(MIA0)]]×100.

Results Obtained

The results of the measurements carried out for groups (I) and (II), namely the ΔMLm, ΔMSAm, ΔMIAm, IML, IMSA and IMIA, are reported in Table 7 below.

TABLE 7

|  | Group (I) | Group (II) |
| --- | --- | --- |
| ΔMLm (mm) | +0.13 | +0.04 |
| IML (%) | 1.0 | 0 |
| ΔMSAm (mm) | +1.14* | +0.35* |
| IMSA (%) | 5.0 | 2.0 |
| ΔMIAm (mm) | +0.42 | −1.19 |
| IMIA (%) | 1.0 | −4.0 |

*Results statistically significant compared with the value at t = 0 (two-sided Student's test assuming unequal variances) with p ≤ 0.05.

The level of increase in the thickness of the hypodermis on the superior-anterior face of the breast (IMSA) of the individuals of group (I), who applied to their breasts the oil-in-water emulsion (E1) comprising N-hexadecanoyl isoleucine, comes to 5%, whereas a value of 2% for this same level of increase in the thickness of the hypodermis on the superior-anterior face of the breast (IMSA) was calculated for the individuals of group (II), who applied to their breasts the oil-in-water emulsion (E2) not comprising N-hexadecanoyl isoleucine.

A mean increase in the thickness of the hypodermis on the superior-anterior face of the breast (ΔMSAm) of 1.14 mm for the individuals of group (I) is also observed, compared with a value of 0.35 mm for the individuals of group (II).

This significant increase in the thickness of the hypodermis on the superior-anterior face of the breast for the individuals of group (I) is accompanied by a stability of the thickness of the hypodermis on the inferior-anterior face of the breast (ΔMIAm=+0.42 mm) and a stability of the thickness of the hypodermis on the lateral side of the breast (ΔMLm=+0.13 mm).

Interpretation of the Results

A mean increase in the thickness of the hypodermis on the lateral side of the breast is considered to be significant when the set of values (ML28i) is statistically different than the values (ML0i).

A mean increase in the thickness of the hypodermis on the superior-anterior face of the breast is considered to be significant when the set of values (MSA28i) is statistically different than the values (MSA0i).

A mean increase in the thickness of the hypodermis on the inferior-anterior face of the breast is considered to be significant when the set of values (MIA28i) is statistically different than the values (MIA0i).

The statistical analysis used to evaluate the significance of these three parameters is a two-sided Student's test assuming unequal variances. Thus, the sets of values (ML28i), (MSA28i) and (MIA28i) are respectively compared with the sets of values (ML0i), (MSA0i) and (MIA0i). An error threshold (p) is set at 5%.

If p is less than or equal to 0.05, the sets of values (ML28i), (MSA28i) and (MIA28i) are considered to be significantly different, respectively, than the sets of values (ML0i), (MSA0i) and (MIA0i). Consequently, it is possible to conclude that there is a significant increase in the thickness of the hypodermis on the lateral side of the breast and/or on the superior-anterior face of the breast and/or on the inferior-anterior face of the breast.

If p is strictly greater than 0.05, the sets of values (ML28i), (MSA28i) and (MIA28i) will not be considered to be significantly different, respectively, than the sets of values (ML0i), (MSA0i) and (MIA0i). Consequently, it will not be possible to conclude that there is a significant increase in the thickness of the hypodermis on the lateral side of the breast and/or on the superior-anterior face of the breast and/or on the inferior-anterior face of the breast.

CONCLUSION

It can therefore be deduced from these results that the presence of N-hexadecanoyl isoleucine in the oil-in-water emulsion (E1) made it possible to increase, in a significant manner, the thickness of the hypodermis on the superior-anterior face of the breast, without this increase occurring to the detriment of the thickness of the hypodermis on the inferior-anterior face of the breast and/or to the detriment of the thickness of the hypodermis on the lateral side of the breast. The use of N-hexadecanoyl isoleucine therefore made it possible to give these individuals a "plumping" effect on their breasts.

b3—Evaluation of the Effect of N-Hexadecanoyl Isoleucine on the Increase in Breast Volume Using the Fringe Projection Technique Protocol These evaluations were carried out on a random subpopulation of 12 volunteers of the population used for the previous evaluations described in sections b1) and b2), which was divided up into 2 equal groups of 6 volunteers (group III and group IV). Each member of group (III) applied emulsion (E1) to both her breasts twice-daily for a period of 28 days and each member of group (IV) applied emulsion (E2) to both her breasts twice-daily for a period of 28 days.

These evaluations consisted in measuring the volume of the breasts of each member (i) of each group before the start of the experiment and at the end of the period of 28 days following the application of emulsions (E1) and (E2).

The experiment consisted in recording a three-dimensional image of the breasts of each member (i) of each group, before and after the application of emulsion (E1) or (E2) for 28 days, using an interference fringe projection profilometer sold under the name 3D Primos Body™. This apparatus, which is characterized by a measurement field of 300 mm×200 mm, by a lateral resolution of 500 micrometers, by a lateral resolution greater than or equal to 30 micrometers and by a data acquisition time greater than or equal to 140 milliseconds, makes it possible to project 2 light beams on to the surface to be analyzed, and the images obtained are recorded by 2 cameras at an angle of 20°. Calculation software integrated into the "3D Primos Body™" then makes it possible to calculate the volume of each area present on the three-dimensional image previously recorded.

For each member (i) of groups (III) and (IV) as defined above, the following are then calculated:
the volume of the breast in question from the three-dimensional image recorded before the start of the experiment (V0i);
the volume of the breast in question from the three-dimensional image recorded at the end of the period of 28 days of the experiment (V28i).

For each member (i) of groups (III) and (IV) as defined above, the change in volume of the breast in question, $\Delta Vi$, is then calculated according to the formula:

$$\Delta Vi=(V28i)-(V0i)$$

Expression of the Results

On the basis of the measurements carried out, indicated above, the following are then calculated for each group:
the mean change in volume of the breast ($\Delta Vm$) according to the formula $$(\Delta Vm)=[\Sigma(\Delta Vi)]/6;$$

the mean of the volume of the breast before the start of the experiment [Mean(V0)] according to the formula:

$$[Mean(V0)]=[\Sigma(MV0i)]/6;$$

the level of increase in the volume of the breast (IV) according to the formula:

$$(IV)=[(\Delta Vm)/[Mean(V0)]]\times 100.$$

Results Obtained

The results obtained for groups (III) and (IV), namely the $\Delta Vm$ and IV, are reported in Table 8 below.

TABLE 8

| | Group (III) | Group (IV) |
|---|---|---|
| ($\Delta Vm$) in cm$^3$ | +2.6* | −0.5* |
| (IV) as % | +1.0%* | 0%* |

*Results statistically significant compared with the value at t = 0 (two-sided Student's test assuming unequal variances) with p ≤ 0.05.

The mean increase in the volume of the breast ($\Delta Vm$) of the individuals of group (III), who applied to their breasts the oil-in-water emulsion (E1) comprising N-hexadecanoyl isoleucine, comes to 2.6 cm$^3$, compared with a change of −0.5 cm$^3$, judged to be nonsignificant, for the individuals of group (IV), who applied to their breasts the oil-in-water emulsion (E2) not comprising N-hexadecanoyl isoleucine. Likewise, the level of increase in the volume of the breast (IV) was calculated at +1.0% for the individuals of group (III), who applied to their breasts the oil-in-water emulsion (E1) comprising N-hexadecanoyl isoleucine, compared with a value of 0% for the individuals of group (IV), who applied to their breasts the oil-in-water emulsion (E2) not comprising N-hexadecanoyl isoleucine.

Interpretation of the Results

A mean increase in the volume of the breast of which the set of values (V28i) is statistically different than the values (V0i) is considered to be significant. The statistical analysis used to evaluate the significance is a Student's test.

The statistical analysis used to evaluate the significance of the increase in breast volume is a two-sided Student's test assuming unequal variances. Thus, the set of values (V28i) is compared with the set of values (V0i). An error threshold (p) is set at 5%.

If p is less than or equal to 0.05, the set of values (V28i) is considered to be significantly different than the set of values (V0i). Consequently, it can be concluded that there is a significant increase in the breast volume. If p is strictly greater than 0.05, the set of values (V28i) will not be considered to be significantly different than the set of values (V0i). Consequently, it will not be possible to conclude that there is a significant increase in the breast volume.

CONCLUSION

It can therefore be deduced from these results that the presence of N-hexadecanoyl isoleucine in the oil-in-water emulsion (E1) made it possible to increase, in a significant manner, the volume of the breasts of the members of group (III).

b4—General Conclusion

The experimental results demonstrated in the experimental sections b1), b2) and b3) demonstrate that the application of a cosmetic composition comprising N-hexadecanoyl isoleucine to the breasts makes it possible, for the individuals in question, to obtain a significant increase in bust measurement, in thickness of the hypodermis on the superior-anterior face of the breast, and in breast volume. Indeed, the use of N-hexadecanoyl isoleucine and the application to the breasts of a cosmetic composition comprising N-hexadecanoyl isoleucine made it possible to generate a "volumizing" effect and a "plumping" effect on the breasts of the individuals in question.

2.2—Demonstration of the Improvement in the Elasticity of the Skin and the "Plumping" Effect of a Cosmetic Composition Comprising N-Hexadecanoyl Isoleucine on the Face of Individuals with Mature Skin a)—Preparation of an Oil-in-Water Emulsion Comprising N-Hexadecanoyl Isoleucine (E3) and of a "Placebo" Oil-in-Water Emulsion (E4)

Emulsions (E3) and (E4) are prepared in the following way:

Step 1): The components of the oily phase and the emulsifying system are successively introduced into a beaker, at a temperature of 80° C., and are subjected to mechanical stirring for a period of 15 minutes, using a stirrer fitted with an "anchor"-type spindle, at a speed of 80 rpm at a temperature of 80° C., so as to form a homogeneous mixture.

Step 2): The thickening polymer is added to the mixture obtained at the end of step 1) at a temperature of 80° C., as is the aqueous phase, prepared beforehand at ambient temperature by mixing its components. The resulting mixture is then subjected to stirring by means of a rotor-stator emulsifying device, sold by the company Silverson, for a period of 4 minutes at a speed of 3000 rpm at a temperature of 80° C.

Step 3): The mixture obtained at the end of step 2) is cooled over a period of 10 minutes to a temperature of 30° C., and kept stirring throughout the cooling by means of a mechanical stirrer fitted with an "anchor"-type spindle, at a speed of 80 rpm.

Step 4): The Sepicide™ LD preservative, the chlorphenesin preservative and the "Petite Fleur" fragrance are then added to the mixture resulting from step 3) at a temperature of 30° C. The pH is then adjusted to a value of 6.0 by adding 50% triethanolamine.

The oil-in-water emulsions (E3) and (E4) have the following compositions (by weight):

TABLE 9

|  | (E3) | (E4) |
|---|---|---|
| Oily phase: | | |
| Plant squalane | 7.00% | 7.00% |
| Polyisobutene | 13.00% | 13.00% |
| Lanol P[(5)] | 1.50% | 1.50% |
| N-hexadecanoyl isoleucine | 1.00% | 0% |
| Thickening polymers | | |
| Sepiplus ™ 400[(6)] | 0.80% | 0.80% |
| Keltrol ™ CGT[(7)] | 0.15% | 0.15% |
| Aqueous phase | | |
| Water | q.s. 100% | q.s. 100% |
| 50% triethanolamine | q.s. pH = 6.0 | q.s. pH = 6.0 |
| Glycerol | 5.00% | 5.00% |
| Emulsifying system | | |
| Montanov ™ 202[(3)] | 2.00% | 2.00% |
| Montanov ™ 82[(8)] | 1.00% | 1.00% |
| Additives | | |
| Sepicide ™ LD[(9)] | 0.70% | 0.70% |
| Petite Fleur fragrance | 0.10% | 0.10% |
| Chlorphenesin[(10)] | 0.30% | 0.30% |

[(5)]Ethylene glycol monopalmitate sold by the company SEPPIC;
[(6)]Self-invertible inverse latex of copolymers such as those described in WO 2005/040230 (INCI name: polyacrylate-13 & polyisobutene & polysorbate 20), sold by the company SEPPIC;
[(7)]Xanthan gum sold by the company CP Kelco;
[(8)]Self-emulsifiable composition based on cetylstearyl alcohol and on cocoglucosides, sold by the company SEPPIC;
[(9)]Phenoxyethanol, preservative sold by the company SEPPIC;
[(10)]Preservative.

b)—Evaluation of the "Plumping" Effect and of the Improvement in the Elasticity of the Skin of the Oil-in-Water Emulsions (E3) and (E4) on the Face of Individuals with Mature Skin The evaluations of the "plumping" effect and of the improvement in the elasticity of the skin, of the oil-in-water emulsions, on the face of individuals with mature skin, are carried out by measuring the following criteria:
 change in the volume of the face at the level of the cheekbone using Primos Body™;
 biomechanical properties of the skin of the face using a Ballistometer™.

The evaluations of the change in the volume of the face at the level of the cheekbone and of the biomechanical properties of the skin of the face were performed on a population of 14 female volunteers, having an average age of 58, with sagging or sunken skin on the face, which was divided up into two equal groups of 7 volunteers (group V and group VI). Each member of group (V) applied emulsion (E3) to her face twice-daily for a period of 56 days, and each member of group (VI) applied emulsion (E4) to her face twice-daily for a period of 56 days.

b1—Evaluation of the "Plumping" Effect of N-Hexadecanoyl Isoleucine on the Face at the Level of the Cheekbone Using the Fringe Projection Technique (Primos Body™)

Protocol

This evaluation consisted in measuring the volume of the face of each member (i) of each group before the start of the experiment and at the end of the period of 56 days following the application of emulsions (E3) and (E4).

The experiment consisted in recording a three-dimensional image of the face of each member (i) of each group, before and after the application of emulsion (E3) or (E4) for 56 days, using an interference fringe projection profilometer sold under the name 3D Primos Body™. This apparatus, which is characterized by a measurement field of 300 mm×200 mm, by a lateral resolution of 500 micrometers, by a lateral resolution greater than or equal to 30 micrometers and by a data acquisition time greater than or equal to 140 milliseconds, makes it possible to project 2 light beams on to the surface to be analyzed, and the images obtained are recorded by 2 cameras at an angle of 20°. Calculation software integrated into the "3D Primos Body™" then makes it possible to calculate the volume of each area present on the three-dimensional image previously recorded.

For each member (i) of groups (V) and (VI) as defined above, the following are then calculated:
 the volume of the cheeks at the level of the cheekbones, from the three-dimensional image recorded before the start of the experiment (W0i);
 the volume of the cheeks at the level of the cheekbones, from the three-dimensional image recorded at the end of the period of 56 days of the experiment (W56i).

Expression of the Results

For each member (i) of groups (V) and (VI) as defined above, the following are then calculated:
 the change in volume of the breast in question, $\Delta Wi$, according to the formula:

$$\Delta Wi = (W56i) - (W0i)$$

the mean change in the volume of the cheeks at the level of the cheekbones ($\Delta Wm$) according to the formula:

$$(\Delta Wm) = [\Sigma(\Delta Wi)]/7$$

Results

The results obtained for groups (V) and (VI), namely the ($\Delta Wm$), are reported in Table 10 below.

TABLE 10

|  | Group (V) | Group (VI) |
|---|---|---|
| ($\Delta Wm$) in ml | +0.784* | +0.276 |

*Results statistically significant compared with the value at t = 0 (two-sided Student's test assuming unequal variances) with $p \leq 0.05$.

The mean increase in the volume of the cheeks at the level of the cheekbones ($\Delta Wm$) of the individuals of group (V), who applied to their cheeks the oil-in-water emulsion (E3) comprising N-hexadecanoyl isoleucine, comes to 0.784 ml, versus an increase of +0.276 ml, considered to be not statistically significant, for the individuals of group (VI), who applied to their cheeks the oil-in-water emulsion (E4) not comprising N-hexadecanoyl isoleucine.

Interpretation of the Results

A mean increase in the volume of the cheeks at the level of the cheekbones of which the set of values (W56i) is statistically different than the values (W0i) is considered to be significant and characteristic of a plumping effect.

The statistical analysis used to evaluate the significance is a Student's test assuming unequal variances. If p is less than or equal to 0.05, the set of values (W56i) is considered to be significantly different than the set of values (W0i). Consequently, it is possible to conclude that there is a significant increase in the volume of the cheeks at the level of the cheekbones. If p is strictly greater than 0.05, the set of values (W56i) will not be considered to be significantly different from the set of values (W0i). Consequently, it will not be possible to conclude that there is a significant increase in the volume of the cheeks at the level of the cheekbones.

CONCLUSION

It can therefore be deduced from these results that the presence of N-hexadecanoyl isoleucine in the oil-in-water emulsion (E3) made it possible to increase, in a significant manner, the volume of the cheeks at the level of the cheekbones of the members of group (V) and therefore to induce a significant "plumping" effect on the face of these individuals of group (V).

b2—Evaluation of the Positive Effect on the Elasticity of the Skin on N-Hexadecanoyl Isoleucine on the Skin of the Face at the Level of the Cheekbone, Using a Ballistometer™ Protocol The study of the biomechanical properties of the skin makes it possible to determine the softening and/or tensioning effects of compositions after they have been applied to the skin.

The existing techniques are based on studying the change in biomechanical properties following an action of suction (use of a Cutometer™), of torsion (Dermal Torque Meter™) or of extension (extensiometer) of the skin or the rebound of a small ball (Ballistometer™) on the skin. These techniques make it possible to obtain precise, fast, reliable results and use protocols that are not traumatic for the skin of the individual.

The skin has 2 rheological characteristics:
an elastic characteristic;
a tension characteristic which varies according to the various areas of the human body.

The rheological properties of the skin are based on its structure, which consists essentially of a three-dimensional network of collagen and of elastin fibers.

To evaluate the effect of N-hexadecanoyl isoleucine on the change in biomechanical properties of the skin of the face at the level of the cheekbone, it was chosen to implement a measurement using a Ballistometer™. The Ballistometer™ makes it possible to illustrate the change in the elastic component of the skin.

The evaluation performed in the context of the present study was carried out with a BLS 780 Ballistometer™ sold by the company Dia-Stron.

The BLS 780 Ballistometer™ consists of a manual probe, connected to a control unit provided with data collection software. The manual probe contains a rigid arm made of aluminum alloy, which is mounted on a torsion shaft, and on the end of said rigid arm is a vibrating sphere which is 2 mm in diameter.

When the vibrating sphere of the probe is brought into contact with the surface of the skin tested, the surface of the skin tested emits a resistance force, which induces an oscillatory movement on the spring of the torsion shaft. This oscillatory movement is then recorded by the control unit and processed by the associated software. This device therefore makes it possible to record the rebounds and the damping thereof, and also the associated energy, obtained after application of the vibrating sphere on the surface of the skin tested.

The software associated with the central unit then makes it possible to calculate various parameters, including the "alpha parameter" which illustrates the rate of attenuation of the mechanical energy. A high value for this "alpha parameter" characterizes a strong elasticity of the surface of the skin tested. An increase over time of the "alpha parameter" attests to firming of the skin.

In the experiment which is the subject of the present study, the biomechanical properties of the skin are evaluated at the level of the cheekbone of the cheek by applying the probe of the Ballistometer™ on said area of the cheekbone of the cheek before and after the application of emulsion (E3) or (E4) for 56 days. Following this application, for each member (i) of groups (V) and (VI) as defined above, the following are then measured:

the "alpha parameter" of the skin of the cheeks at the level of the cheekbones before the start of the experiment ($\alpha 0i$), the "alpha parameter" of the skin of the cheeks at the level of the cheekbones at the end of the period of 56 days of the experiment ($\alpha 56i$).

Expression of the Results

For each member (i) of groups (V) and (VI) as defined above, the following are then calculated:

the change in the "alpha parameter" of the skin of the cheeks at the level of the cheekbones, ($\Delta\alpha i$), according to the formula:

$$(\Delta\alpha i)=(\alpha 56i)-(\alpha 0i)$$

and for each group:

the mean change in the "alpha parameter" of the skin of the cheeks at the level of the cheekbones, ($\Delta\alpha m$), according to the formula:

$$(\Delta\alpha m)=[\Sigma(\Delta\alpha i)]/7$$

the mean of the "alpha parameter" of the skin of the cheeks at the level of the cheekbones before the start of the experiment, [Mean($\alpha 0$)], according to the formula:

$$[Mean(\alpha 0)]=[\Sigma(M\alpha 0i)]/7$$

the degree of change of the "alpha parameter" of the skin of the cheeks at the level of the cheekbones, ($C\alpha$), according to the formula:

$$(C\alpha)=(\Delta\alpha m)/[Mean(\alpha 0)]\times 100$$

Results Obtained

The results obtained for groups (V) and (VI), namely the mean changes of the "alpha parameter" of the skin of the cheeks at the level of the cheekbones ($\Delta\alpha m$) and the degree of change of the "alpha parameter" of the skin of the cheeks at the level of the cheekbones ($C\alpha$), are reported in Table 11 below.

TABLE 11

|  | Group (V) | Group (VI) |
|---|---|---|
| ($\Delta\alpha m$) | −0.005* | 0.0 |
| ($C\alpha$) as % | −10.0%* | +1.0% |

*Results statistically significant compared with the value at t = 0 (two-sided Student's test assuming unequal variances) with p ≤ 0.05.

The mean change in the "alpha parameter" of the skin of the cheeks at the level of the cheekbones ($\Delta\alpha m$) of the individuals of group (V), who applied to their cheeks the oil-in-water emulsion (E3) comprising N-hexadecanoyl isoleucine, is −0.005, compared with no change (($\Delta\alpha m$)=0) for the individuals of group (VI), who applied to their cheeks the oil-in-water emulsion (E4) not comprising N-hexadecanoyl isoleucine.

Likewise, the degree of change in the "alpha parameter" of the skin of the cheeks at the level of the cheekbones ($C\alpha$) was evaluated at −10% for the individuals of group (V), versus +1.0% for the individuals of group (VI).

Interpretation of the Results

A mean increase in the "alpha parameter" of which the set of values ($\alpha 56i$) is statistically different than the values ($\alpha 0i$) is considered to be significant and characteristic of an improvement in the elasticity of the skin of the cheeks at the level of the cheekbones. The statistical analysis used to evaluate the significance is a Student's test assuming unequal variances. If p is less than or equal to 0.05, the set of values ($\alpha 56i$) is considered to be significantly different than the set of values ($\alpha 0i$). Consequently, it can be concluded that there is a significant increase in the elasticity of the skin of the cheeks at the level of the cheekbones. If p is strictly greater than 0.05, the set of values ($\alpha 56i$) will not be considered to be significantly different than the set of values ($\alpha 0i$). Consequently, it will not be possible to conclude that there is a significant increase in the elasticity of the skin of the cheeks at the level of the cheekbones.

CONCLUSION

It can thus be deduced from these results that the presence of N-hexadecanoyl isoleucine in the oil-in-water emulsion (E3) made it possible to induce, in a significant manner, an improvement in the elasticity of the skin of the cheeks at the level of the cheekbones of the members of group (V).

b3—General Conclusion

The experimental results demonstrated in experimental sections b1) and b2) of the present chapter 2.2 show that the application of a cosmetic composition comprising N-hexadecanoyl isoleucine to the face makes it possible, for the individuals in question, to induce a "plumping" effect and an improvement in the elasticity of the skin of the cheeks at the level of the cheekbones, in a significant manner.

LITERATURE REFERENCES CITED IN THE DESCRIPTION

Dumont et al.: Analysis of the implications of the adipose tissue in facial morphology, from a revue of the literature and dissections of 10 half-faces. Annales de chirurgie plastique esthétique [Annals of cosmetic plastic surgery]. 2007; 52: 169-205.

Fève et al.: La différenciation adipocytaire: tout un programme . . . M/S [Adipocyte differentiation: an entire program . . . M/S]. 1998; 14: 848-57.

Gregoire et al.: Understanding adipocyte differentiation. Physiological reviews. 1998, July; 78 (3): 783-809.

Guo et al.: Aging results in paradoxical susceptibility of fat cell progenitors to lipotoxicity. Am J Physiol. Endocrinol. Metab. 2006, December: 1-54.

Karagiannides et al.: Altered expression of C/EBP family members results in decreased adipogenesis with aging. Am J Physiol Regulatory Integrative Comp Physiol. 2001, January; 280: R1772-80.

Karagiannides et al.: Increased CUG triplet repeat-binding protein-1 predisposes to impaired adipogenesis with aging. J Biol Chem. 2006, August; 281 (32): 23025-33.

Kirkland et al.: Adipogenesis and aging: does aging make fat go MAD? Exp Gerontol. 2002, June; 37(6): 757-67.

Smith et al.: The adipocyte life cycle hypothesis. Clinical Science. 2006; 110: 1-9.

Yu et al.: Chronological changes in metabolism and functions of cultured adipocytes: a hypothesis for cell aging in mature adipocytes. Am J Physiol Endocrinol Metab. 2004, March; 286: 402-410.

The invention claimed is:

1. A cosmetic treatment process for obtaining a "volumizing" and/or "plumping" effect on the skin of a part of the human body chosen from the breasts, the face, the cheeks, the buttocks and the eyelids, characterized in that it consists in applying to said part a cosmetic composition comprising an effective amount of N-hexadecanoyl isoleucine, wherein the effective amount of N-hexadecanoyl isoleucine is between 0.000001% and 0.05% by weight.

* * * * *